(12) United States Patent  
Zhang

(10) Patent No.: US 7,550,652 B2  
(45) Date of Patent: Jun. 23, 2009

(54) WATERMELON POLLENIZER SP-4

(75) Inventor: Xingping Zhang, Woodland, CA (US)

(73) Assignee: Syngenta Participations AG, Basel (CH)

( * ) Notice: Subject to any disclaimer, the term of this patent is extended or adjusted under 35 U.S.C. 154(b) by 126 days.

(21) Appl. No.: 11/633,376

(22) Filed: Dec. 4, 2006

(65) Prior Publication Data

US 2008/0134368 A1 Jun. 5, 2008

(51) Int. Cl.
  *A01H 5/00* (2006.01)
  *A01H 5/10* (2006.01)
  *A01H 1/00* (2006.01)
(52) U.S. Cl. ...................................... 800/308; 800/260
(58) Field of Classification Search ........................ None
  See application file for complete search history.

(56) References Cited

U.S. PATENT DOCUMENTS

| | | | | |
|---|---|---|---|---|
| 5,007,198 | A | 4/1991 | Gray et al. | 47/58 |
| 6,355,865 | B1 | 3/2002 | Elmstrom | 800/308 |
| 6,759,576 | B2 | 7/2004 | Zhang et al. | 800/308 |
| 2003/0121075 | A1 | 6/2003 | Barham | 800/308 |
| 2003/0163852 | A1 | 8/2003 | Barham et al. | 800/308 |
| 2006/0168701 | A1 | 7/2006 | Zhang | 800/308 |
| 2006/0200880 | A9 * | 9/2006 | Barham | 800/308 |

FOREIGN PATENT DOCUMENTS

WO  WO 00/70933  11/2000

OTHER PUBLICATIONS

M.S. Buttrose and M. Sedgley, "Some effects of Light Intensity, Daylength and Temperature on Growth of Fruiting and Non-fruiting Watermelon (*Citrullus lanatus*)," *Ann. Bot.*, vol. 42, 599-608, 1978.
J.M. Crall et al, "SSDL: A High-quality Icebox Watermelon Breeding Line Resistant to Fusarium Wilt and Antracnose," *HortScience*, 29(6), 707-708, 1994.
Fan Min et al., "Identification of Quantitative Trait Loci Associated with Fruit Traits in Watermelon [*Citullus Ianantus* (Thanb) Mansf] and Analysis of Their Genetic Effects," *Acta Genetica Sinica*, 27(10), 902-910, 2000.
Gabriele Gusmini and Todd C. Wehner, "Foundations of Yeild Improvement in Watermelon," *Crop Sci.*, 45, 141-146, Jan.-Feb. 2005.
D.M. Hegde, "Physiological Analysis of Growth and Yield of Watermelon (*Citrullus lanatus* Thunb Musf) in Relation to Irrigation and Nitrogen Fertilization," *J. Agronomy & Crop Science*, 160, 296-302, 1988.
G.J. Hochmuth, et al. "Cultural Management" in *Watermelons: Characteristics, Production, and Marketing* (Virginia, ASHS Press, 2001), 78-97.
Yasutaka Kano, "Effects of summer day-time temperature on sugar content in several portions of watermelon fruit (*Citrullus lanatus*)," *Journal of Horticultural Science & Biotechnology*, 79(1), 142-145, 2004.

Karchi, Z. et al., "The Importance of Cultural Practices in Materializing Yield Potential in a Tetraploid Watermelon Cultivar," *Cucurbit Genetics Cooperative Report*, 6, 59-61, 1983.
Ivan J. Kenny and D.R. Porter, "Relative Rind Toughness Among Watermelon Varieties," *American Society for Horticultural Science*, vol. 38, 537-540, 1941.
*Known-You Seed Co., Ltd.*, (Kaohsiung, Taiwan), [catalog], 1991/1992, pp. 22.
*Known-You Seed Co., Ltd.*, (Kaohsiung, Taiwan), [catalog], 1994, pp. 2.
D.M. Maynard and G.W. Elmstrom, "Triploid Watermelon Production Practices and Varieties," *Acta Horticulture*, 318, 169-178, 1992.
D. Scott NeSmith and John R. Duval, "Fruit Set of Triploid Watermelons as a Function of Distance from a Diploid Pollinizer," *HortScience*, 36(1), 60-61, Feb. 2001.
John M. Poehlman and David A. Sleper, "Quantitative Inheritance," In Breeding Field Crops, 4th ed., Iowa State University Press, Ames, p. 71, (1995).
C.F. Poole, "Genetics of Cultivated Cucurbits," *The Journal of Heredity*, 35, 122-128, 1944.
D.R. Porter, "Inheritance of Certain Fruit and Seed Characters in Watermelons," *Hilgardia*, 10(12), 489-509, Jan. 1937.
Bill Rhodes and Fenny Dane, "Gene List for Watermelon," *Cucurbit Genetics Cooperative Report*, 22, 61-77, 1999.
W.D. Scott et al., "Calcium Fertilization and Cultivar Affect Watermelon Rind Thickness and Resiliency," *Hortscience*, 25(9), 1075, Sep. 1990.
Keita Sugiyama et al., "Relationship between Rind Hardness and Rind Tissue Structure in Watermelon," *J. Japan. Soc. Hort. Sci.*, 68(1), 108-116, 1999.
F.J. Sundstrom et al., "Influence of K and Ca on Quality and Yield of Watermelon," *J. Amer. Soc. Hort. Sci.*, 108(5), 879-881, 1983.
Ignacio Susin et al., Fertility and Pollen Tube Growth in Polyploid Melons (*Cucumis melo L.*), *Euphytica*, 93, 369-373, 1997.
Watermelon (and Stockmelon, Pie Melon, or Citron Melon) in Insect Pollination of Cultivated Crop Plants by S.E. McGregor, USDA, originally published 1976, [online] [Internet: >URL: http://gears.tucson.ars.ag.gov/book/chap6/watermelon.html] retrieved Feb. 6, 2002.
Wagner Force Measurement Instruments, [catalogue] [online]. [Internet: >URL: http://www.wagnerinstruments.com/] retrieved Jan. 13, 2004.
Wagner Force Measurement Instruments, [Wagner Fruit Test™ online manual]. [Internet: >URL: http://www.wagnerforce.com/manuals/ftmanual.pdf] retrieved Jan. 13, 2004.
S. Wolf et al., "Genetic Variability in Flower Attractiveness to Honeybees (*Apis mellifera L.*) within the Genus *Citrullus*," *HortScience*, 34(5), 860-863, 1999.

* cited by examiner

*Primary Examiner*—Anne R Kubelik
(74) *Attorney, Agent, or Firm*—S. Matthew Edwards

(57) ABSTRACT

The present invention provides a novel watermelon line designated SP-4, and method for pollinating seedless watermelon plants. The present invention also provides methods for producing triploid, seedless watermelon fruit.

24 Claims, No Drawings

WATERMELON POLLENIZER SP-4

FIELD OF THE INVENTION

This invention is in the field of watermelon breeding, specifically relating to a watermelon line. In one aspect, the watermelon line is used to pollinate triploid watermelon plants for the commercial production of seedless watermelon fruit.

BACKGROUND OF THE INVENTION

Watermelon is an important horticultural crop that accounts for 2% of the world area devoted to vegetable crops. There were 6,024,000 acres of watermelon grown in the world and 187,000 acres of watermelons grown in the United States in 1997 (FAO Production Yearbook 51, 1998). The estimated annual world watermelon value exceeded $7.6 billion when using the United States average price for 1995-1997. The United States watermelon crop amounted to over 41 million cwt, from over 174,000 harvested acres, and a farm value of over $266 million, accounted for 9.2% of the harvested acres, 10.0% of the production, and 3.5% of the value of the United States fresh vegetable industry in 1999 (USDA Agricultural Statistics 2001). California was the leading state in watermelon farm gate value, exceeded $72 million in 2000, due to high percentage of triploid seedless watermelon grown in California. Seedless watermelon receives well above the average price for seeded watermelons in the market. According to National Watermelon Promotion Board, over 80% watermelons sold in the super-market are seedless watermelon in 2006 in the United States of America.

The goal of plant breeding is to combine in a single variety or hybrid various desirable traits. Desirable traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate and maturity, are important. Other desired traits may include particular nutrient content, color, fruit shape, as well as taste characteristics.

As with many different plants, a watermelon plant contains a fruit part and a plant part. Each part contains different traits that are desired by consumers and/or growers, including such traits as flavor, texture, disease resistance, and appearance traits such as shape and color. The seedless trait in the watermelon fruit is highly desired by consumers. For production of seedless watermelon, optimum pollination characteristics of the pollinating plant are desired.

Seedless watermelon plants are triploid and must be pollinated by the pollen of diploid watermelon plants. To provide adequate pollenization of seedless watermelon plants, it is current practice to plant diploid pollenizer plants over approximately 25-33% of the field surface. The remaining portion of the field is planted with the triploid plants. Thus, to maximize the value of the crop in the field, growers use high yield marketable diploid watermelon varieties, which ultimately compete with the triploid seedless varieties for sun, nutrients, and space. The present invention recognizes the need to increase the pollenizing capacity of diploid watermelon plants in order to decrease the ratio of diploid to triploid plants in the field, thereby increasing the yield of the seedless watermelon. The present invention further recognizes the need for phenotypic characteristics of the diploid pollenizer plants, which permit these diploids to be planted in close proximity to the triploid plants and to share the field surface with the triploid plants, thereby effectively decreasing the surface area of the field required for the diploid pollenizers of the invention. The present invention also further recognizes the need for pollenizer plants with improved resistance to diseases.

SUMMARY OF THE INVENTION

The present invention provides a novel watermelon line designated SP-4. The present invention also provides methods for pollinating seedless watermelon plants using plants of watermelon line SP-4. The present invention also provides methods to produce triploid seedless watermelon fruits and uses of the novel watermelon line to improve current methods of commercial production of seedless watermelon and to increase the yield of seedless watermelon fruit.

According to the invention, watermelon line SP-4 is resistant to *Fusarium* wilt race 1 (Fon 1) and to Anthracnose race 1 (Col 1), and tolerant to *Fusarium* wilt race 2 (Fon 2). In another aspect of the invention, watermelon line SP-4 is a diploid watermelon inbred line.

According to the invention, watermelon line SP-4 has a high number of open (lacy) branches. The openness of the branched or lacy vine results, in part, from the distinct small and non-overlapping, deep lobed leaves. The lacy branches and small, non-overlapping, deep lobed leaves of the invention provide more access of bees to the flowers of both the pollenizing and the triploid plant, thereby enhancing transfer of the pollen from plants of watermelon line SP-4 to the female flowers of the triploid watermelon plants. A second advantage of small leaves characterized by deep, non-overlapping lobes is that more sunlight is able to penetrate to adjacent triploid plants. The third advantage of small leaves characterized by deep, non-overlapping lobes is that these leaves take up less field area.

Also according to the present invention, watermelon line SP-4 comprises small fruits with brittle rind. The small fruits with brittle rind reduce the load to the plant and allow the plant to continue flowering for extended periods of time. The long flowering duration of the plants of watermelon line SP-4 results in increased fruit set and yield of seedless watermelon.

The fruits of watermelon line SP-4 weigh approximately in the range of 1.5 to 3.5 kg, especially approximately 2 kg. The rind of the fruits of watermelon line SP-4 is brittle. In one embodiment, the rind of the fruits of watermelon line SP-4 breaks under a pressure in the range of about 800 g to about 1,500 g when a fruit tester with a 2 mm tip is used.

In one embodiment, plants of watermelon line SP-4 comprise, at maturity, the characteristics of smaller fruit and leaf size compared to the watermelon variety Mickylee. The leaves of watermelon line SP-4 have deep, non-overlapping lobes, wherein the fruit rind is more brittle than the rind of the variety Mickylee. The skin color of the fruits of watermelon line SP-4 is light green. In one embodiment, it is different from the skin color of the fruits of most commercially grown seeds watermelon varieties.

In one embodiment, the present invention discloses a method for producing triploid, seedless watermelon fruit comprising the steps of inter-planting a seed or a plant of watermelon inbred line SP-4 and seed or plants of triploid watermelon plants in a field; and allowing pollination of said triploid watermelon plants by pollen of said plant of watermelon inbred line SP-4 to obtain triploid, seedless watermelon fruit. In one embodiment, the method further comprises harvesting seedless watermelon fruit from triploid plants.

The present invention also provides a method for inter-planting plants of watermelon line SP-4 amongst the triploid watermelon plants in a field. The invention also provides a method of increasing the yield of triploid seedless watermelon plants by plants of watermelon inbred line SP-4, wherein the fruit are not harvested for human consumption.

In one embodiment, the present invention discloses a method of producing seeds of watermelon inbred line SP-4 comprising growing a plant of watermelon inbred line SP-4; allowing pollination of said plants, for example open-pollination of said plants in an isolated plot/field; and harvesting seeds from said plants. In one embodiment, the method further comprises washing and drying said seed.

In one embodiment, the present invention discloses a method of vegetative propagating watermelon inbred line SP-4 comprising collecting shoot tissue of a plant of watermelon inbred line SP-4; cultivating said tissue to obtain proliferated shoots; rooting said proliferated shoots to obtain rooted plantlets. In one embodiment, the method further comprises growing plants from said rooted plantlets. In one embodiment, the method further comprises harvesting seeds from said plants. In one embodiment, the method further comprises washing and drying said seed.

DETAILED DESCRIPTION OF THE INVENTION

Development of Seedless Watermelons

Triploid watermelons are created by crossing a tetraploid (4X) female line with diploid (2X) male line. The resulting triploid (3X) watermelon seed are planted in a field with diploid watermelon pollenizers. The resulting fruit of the triploid watermelon are seedless.

To create a tetraploid female watermelon line, it is known in the art to use chemicals that alter mitosis of a diploid inbred line so that unusual numbers of chromosomes are obtained. For example, colchicine is a chemical that alters the mitotic spindle fibers of diploid cells resulting in a number of cells that are tetraploid. The diploid line used to create a tetraploid is selected based on the traits desired for the tetraploid line. Traits that are desired for a tetraploid line may therefore first be introgressed into the diploid inbred lines that will be used to develop the tetraploid lines by breeding methods well known to those skilled in the art. Thus, the diploid and tetraploid parent lines are bred separately for the desired traits.

It usually requires at least two generations of self-pollination and selection to "fix" the 4X condition, after the colchicine treatment generation because, often, chromosomal aberrations are encountered that affect seed fertility, and must be eliminated. Once the stable tetraploid containing the desired characteristics is verified, it then can be used as a stable female parent for the production of the triploid hybrid. A stable diploid inbred is selected for use as the male parent. Methods for developing tetraploid plants are described in Kihara, H., 1951, Triploid Watermelons, *Proceedings of American Society for Horticultural Science* 58:217-230; and Eigsti, O. J., 1971, Seedless Triploids, HortScience 6, pgs. 1-2.

The tetraploid female and diploid male are planted in a seed production field. The pollen of the diploid male parent is transferred to the female tetraploid flower by methods well known to those skilled in the art. The triploid seed that is produced is present in the resulting fruit and is planted to produce the triploid plants. The breeding of watermelon is further described in Mark Bassett (Editor), 1986, Breeding Vegetable Crops, AVI Publishing, ISBN 0-87055-499-9.

A triploid seedless watermelon is a true F1 hybrid between a tetraploid watermelon, as the female parent, and a diploid watermelon, as the male parent (Kihara, H. 1951. Triploid Watermelons. *Proceedings of American Society for Horticultural Science* 58:217-230). The seedless condition in triploid watermelon is the result of the presence of three homologous sets of chromosome per somatic cell rather than the usual two. Cells with three sets of homologous chromosomes are said to be triploid and are designated as 3X. The triploid seedless watermelons have 33 chromosomes (2N=3X=33) in their somatic cells. The inability of the triploid zygote to produce normal viable gametes (pollen and egg cells) causes the absence of seeds in triploid fruits. Typically, seedless watermelons contain small edible white ovules, similar to those in immature cucumbers.

Adequate viable pollen supply from the diploid pollenizer watermelon is essential for the triploid female flowers to set and develop into regular seedless fruit. The female flowers of triploid watermelon will not set if they are not pollinated by viable pollen of diploid watermelon. (Maynard, D. N. (editor), 2001, *Watermelons: Characteristics, Production and Marketing*, ASHS Press, ISBN 0-9707546-1-2). The diploid watermelon grown in a field of triploid plants is referred to herein as the "pollenizer."

Development of Watermelon Line SP-4

Watermelon line SP-4 (also referred herein as "SP-4") was developed as a pollenizer for triploid watermelon in the production of triploid seedless watermelon. SP-4 was developed at Syngenta Seeds' Research Stations in Woodland, Calif. and Naples, Fla., as a result of traditional recombination breeding. SP-4 comprises resistance to *Fusarium* wilt and anthracnose when compared to Syngenta watermelon variety SP-1. Watermelon variety SP-1 is subject to Plant Variety Protection Certificate Number: 200300006 and to U.S. Pat. No. 6,759,576, and is also referred herein as "SP-1".

The chronological description of the development of SP-4 is outlined below. The F4 line F4(TO×ESW1) that was used for developing SP-1 was crossed, in the greenhouse in the summer of 2002 at Woodland station, with the *Fusarium* wilt resistant Plant Introduction PI 296341FR to introduce the resistances to *Fusarium* wilt race 0, 1 and race 2 (Fon 0, Fon 1 & Fon 2) (MARTYN R D, NETZER D. 1991. *Resistance to races 0, 1, and 2 of Fusarium wilt of watermelon in Citrullus sp.* PI 296341-FR. *HortScience* 26(4): 429-432). In the fall of 2002, the F1 was further crossed with a breeding line F6(TO) with brittle rind to insure the presence of brittle rind gene "e" in the population.

The F2 and F3 progenies were screened for the resistances to Fon 1 and Fon 2 in the greenhouse at Woodland station. The resistant plants with required plant characteristics were self-pollinated. The F4 lines were selected and self-pollinated in the field at Naples station in the fall of 2003. In the spring of 2004 the selected F4 lines were crossed with a Syngenta watermelon inbred line 90-4195 in the greenhouse at Woodland station. This is to add Anthracnose race 1 (Col 1) resistance and better adaptability to the population. The resulted F1's were further crossed with di-haploid line of SP-1, SP-1DH, to insure the presence of the desirable characteristics of leaf, vine, flowering and fruit of SP-1 in the breeding population. The F2 and F3 progenies were screened for resistance to Fon 1 and Col 1, and selected for desirable characteristics as outlined above, in the fall of 2004 and spring of 2005 at Naples station.

The F4 lines were evaluated and the selected lines were self-pollinated in the field of Woodland station in the summer of 2005. The F4 lines were also tested for resistance to Fon 1, Fon 2 and Col 1 in the greenhouse at Woodland station. The F5 lines were further tested and self-pollinated in the fall of 2005 at Naples station. The same set of F5 lines were also screened for resistance to Fon 1 and Col 1 in the greenhouse at Woodland station. The resistant lines/plants were self-pollinated in the greenhouse.

In the spring of 2006, the best 6 lines of F6 were evaluated at Naples station against SP-1 and Mickylee with replicated trials. The same 6 lines were further screened for resistance to Fon 2 in the greenhouse at Woodland station. The resistant plants were self-pollinated to produce F7 lines. In the greenhouse the line 6SpHG66 had the best resistance to Fon 2 and best tolerance to powdery mildew. The line 6SpHG66 was also genetically uniform for the 230 plants observed. In the field, the same line had the best uniformity for plant, flowering and fruit characteristics. Therefore, the seed of line 6SpGH66 were bulk harvested and the line with pedigree of ((F2(TO×ESW1)F2-4-B1×PI296341)×((TO)F2-1-4-1-2)-5: 1/90-4195:10//SP1DH-4:B—)1-2-1-B—B— was promoted to the finished line SP-4.

In the summer of 2006 the same 6 lines (as tested at Naples station in the spring) were evaluated in the open field at Woodland station using SP-1 and Mickylee as checks with replicated trials. Similar to the spring Naples trials, the selected SP-4 line had best uniformity.

In the summer of 2006, 600 plants of the SP-4 line were grown in net-cage for foundation seed increase and over 10,000 plants of SP-4 line were grown in isolated open field for commercial seed production. The line is genetically stable and uniform for the characteristics of small leaf, deep leaf lobe, early flowering, fine (lacy) branches, small fruit, grayish skin with fine lines, brittle rind, white flesh and small seeds.

Accordingly, in one embodiment, the present invention provides a diploid watermelon inbred line designated SP-4.

The quick development and stabilizing of watermelon SP-4 were due mainly to the recessive feature of most of the traits concerned.

Compared to SP-1, watermelon line SP-4 is new and unique for the following characteristics:

1. SP-4 has much smaller seed size than SP-1, 60+/−3 seed/gram versus 21+/−2 seed/gram.
2. SP-4 is resistant to *Fusarium* wilt race 1 (Fon 1) (see Table 1), but SP-1 is susceptible to Fon 1.
3. SP-4 is resistant to Anthracnose race 1 (Col 1) (see Table 2), but SP-1 is susceptible to Col1.
4. SP-4 is tolerant to *Fusarium* wilt race 2 (Fon 2) (see Table 3), while SP-1 and any other commercial watermelons are highly susceptible to Fon 2.

TABLE 1

Test of Resistance to *Fusarium* wilt Race 1 (Fon 1) in line SP-4 and Rootstocks

| Variety | Type | Species | Isolate Used | Total Plant Inoculated | R | S | Results |
|---|---|---|---|---|---|---|---|
| Ojakkyo | Rootstock | *Citrullus lanatus* var. *citroides* | Race 1 (811B) | 66 | 64 | 2 | Resistant |
| Emphasis | Rootstock | *Lagenaria siceraria* | Race 1 (811B) | 30 | 30 | | Resistant |
| BN111 | Rootstock | *Cucurbita maxima* x *C. moschata* | Race 1 (811B) | 72 | 72 | | Resistant |
| BN911 | Rootstock | *Cucurbita maxima* x *C. moschata* | Race 1 (811B) | 72 | 72 | | Resistant |
| StrongTosa | Rootstock | *Cucurbita maxima* x *C. moschata* | Race 1 (811B) | 72 | 72 | | Resistant |
| SP-4 | Pollenizer | *Citrullus lanatus* var. *lanatus* | Race 1 (811B) | 66 | 66 | | Resistant |
| Calhoun Grey | Check | *Citrullus lanatus* var. *lanatus* | Race 1 (811B) | 20 | 20 | | Resistant |
| Black diamond | Check | *Citrullus lanatus* var. *lanatus* | Race 1 (811B) | 20 | | 20 | Susceptible |

Standard *Fusarium* wilt resistant test protocol was used for this test. The test was conducted in the pathology greenhouse of Woodland station and was finished on Aug. 8, 2006. "R"=resistant plants, "S"=susceptible plants. Watermelon line SP-4 is highly resistant to *Fusarium* wilt race 1 (Fon 1).

TABLE 2

Test of Resistance to Anthracnose in line SP-4

| Variety | Isolate Used | Total Plant Inoculated | 1 (no spots) | 2 (<10% spots) | 3 (11 to 20%) | 4 (21-39%) | 5 (dead) | Results |
|---|---|---|---|---|---|---|---|---|
| SP-4 | Coll (6324) | 126 | 126 | 0 | 0 | 0 | 0 | Resistant |
| Charleston Grey | Coll (6324) | 20 | 12 | 3 | 3 | | 2 | Resistant |
| Calhoun Grey | Coll (6324) | 40 | 0 | 0 | 0 | 0 | 40 | Susceptible |

Standard Anthracnose test was used for this test. The test was conducted in the pathology greenhouse of Woodland station and was finished on Aug. 8, 2006. Variety Charleston Grey is the resistant check and Calhoun Grey is the susceptible check. Watermelon line SP-4 is highly resistant to Anthracnose race 1 (Col 1).

TABLE 3

Test of Resistance to *Fusarium* wilt Race 2 in SP-4 and Rootstocks

| Variety | Type | Species | Isolate Used | Total Plant Inoculated | R | S | Results |
|---|---|---|---|---|---|---|---|
| J008 | Rootstock | *Lagenaria siceraria* | Race 2 (CalG) | 72 | 72 | | Resistant |
| Emphasis | Rootstock | *Lagenaria siceraria* | Race 2 (CalG) | 36 | 36 | | Resistant |
| BN111 | Rootstock | *Cucurbita maxima* x *C. moschata* | Race 2 (CalG) | 72 | 72 | | Resistant |
| BN911 | Rootstock | *Cucurbita maxima* x *C. moschata* | Race 2 (CalG) | 72 | 72 | | Resistant |
| Strong Tosa | Rootstock | *Cucurbita maxima* x *C. moschata* | Race 2 (CalG) | 72 | 72 | | Resistant |
| Ojakkyo | Rootstock | *Citrullus lanatus* var. *citroides* | Race 2 (CalG) | 72 | 14 | 58 | Susceptible |
| SP-1 | Pollenizer | *Citrullus lanatus* var. *lanatus* | Race 2 (CalG) | 36 | 1 | 35 | Susceptible |
| SP-4 | Pollenizer | *Citrullus lanatus* var. *lanatus* | Race 2 (CalG) | 72 | 40 | 32 | Tolerant |
| PI296341-FR | Check | *Citrullus lanatus* var. *citroides* | Race 2 (CalG) | 72 | 50 | 22 | Tolerant |
| Calhoun Grey | Check | *Citrullus lanatus* var. *lanatus* | Race 2 (CalG) | 20 | | 20 | Susceptible |
| Sugar Baby | Check | *Citrullus lanatus* var. *lanatus* | Race 2 (CalG) | 20 | | 20 | Susceptible |
| Charleston Grey | Check | *Citrullus lanatus* var. *lanatus* | Race 2 (CalG) | 20 | | 20 | Susceptible |

Standard *Fusarium* wilt test protocol was used for this test. The test was conducted in the pathology greenhouse of Woodland station and was finished on Aug. 8, 2006. "R"=resistant plants, "S"=susceptible plants. *Fusarium* wilt race 2 (Fon 2) is the most virulent race we know. No resistance to this race is available in any commercial watermelon variety. The resistance to Fon 2 is low even in the reported resistant source PI296341-FR (MARTYN R D, NETZER D. 1991. *Resistance to races 0, 1, and 2 of Fusarium wilt of watermelon in Citrullus sp. PI 296341-FR. HortScience* 26(4): 429-432), as shown in our test. Watermelon line SP-4 is tolerant to Fon 2 while the Fon 1 resistant check Calhoun Grey and the rootstock Ojakkyo are susceptible to Fon 2.

The development of watermelon line SP-4 maintained all the desirable traits of SP-1 by using the line that became SP-1 as the initial parent and then backcrossed the advanced lines to SP-1. The variety SP-4 has the same type of small leaf and deep leaf lobe. The fruit of SP-4 is also brittle and small, similar to the fruit of SP-1 (Table 4). The fruit grown at Woodland station during the hot summer had higher brix (as measured by using hand hold Refractometer), smaller fruit size and more durable rind, compared to those grown in the Spring at Naples station with cooler temperatures and wet weather. The flowering and branching habits of SP-4 are the same of SP-1. The fruit phenotype of SP-4 is very similar to the fruit of SP-1. Emergence to anthesis for SP-4 typically occurs approximately 4 days later than for SP-1. Pollination to maturity for SP-4 is typically approximately 1 day earlier than for SP-1.

Watermelon line SP-4 was developed to be a pollenizer for the triploid watermelon to produce seedless watermelon fruit. Because of the unique plant and fruit characteristics, much better resistance, and the broader genetic background, watermelon line SP-4 is a superior pollenizer for seedless watermelon production. Growers can get at least 25-33% more seedless fruit compared to what they are doing with standard diploid watermelon as pollenizer. Growers can freely select the best seedless varieties for their production programs when watermelon line SP-4 is used as pollenizer because of its distinct fruit size, color and shape compared to commercial triploid watermelons. Using watermelon line SP-4 as pollenizer growers can increase the yield potential of their triploid watermelon because of the simplified field management and prolonged flowering periods of plants of watermelon line SP-4.

TABLE 4

Fruit Characteristics of SP-4 and the Checks Grown at Woodland and Naples Station in 2006 Spring (Naples) and Summer (Woodland)

| Variety | Location** | Brix | Fruit Wt (kg) | Rind Firmness (g)* |
|---|---|---|---|---|
| SP-4 | Woodland | 9.0 +/− 0.0 | 1.85 +/− 0.11 | 1117 +/− 42 |
| SP-1 | Woodland | 8.5 +/− 0.3 | 2.05 +/− 0.08 | 1305 +/− 107 |
| Mickylee | Woodland | 13.2 +/− 0.2 | 4.87 +/− 10.59 | >3000 |
| SP-4 | Naples | 5.7 +/− 0.2 | 2.07 +/− 0.05 | 913 +/− 22 |
| SP-1 | Naples | 5.8 +/− 0.1 | 2.04 +/− 0.14 | 975 +/− 96 |
| Mickylee | Naples | 12 +/− 0.3 | 5.58 +/− 0.30 | 3003 +/− 164 |

*Rind Firmness are measured with a Wagner Fruit Test ™ FT11 using a 2 mm probe for the fruits grown at Naples station and with Wagner Fruit Test ™ FT5 using a 2 mm probe for the fruits grown at Woodland station.
**Naples crop was transplanted on Feb. 28, 2006 at Naples station with plastic mulched high bed.
Woodland crop was transplanted on May 23, 2006 at Woodland station with semi-high bare bed.

Plant: Watermelon line SP-4 is monoecious. Cotyledons of plants of watermelon line SP-4 are flat. Typically, at first fruit set, there are approximately 7 main stems at crown per plant, and approximately 12 staminate and 4 pistillate flowers per plant. The stem of plants of watermelon line SP-4 is round and pubescent, with a diameter of approximately 4 mm at second node. Typically, the ratio of vine length (cm) by number of internodes (at last harvest) is approximately 12.

Leaf: The leaves of plants of watermelon line SP-4 are significantly smaller with deep, non-overlapping leaf lobes and are more numerous than that variety Sangria™. The surface area of the leaf of plants of watermelon line SP-4 is approximately 5 to 12 times less than the surface area of the typical diploid pollenizer, Sangria™ plant. The small, deeply lobed and non-overlapping leaves of plants of watermelon line SP-4 allow more sunlight through to adjacent triploid watermelon plants. Leaves of watermelon line SP-4 are obovate and longer than wide. The dorsal and ventral surface of the leaves are pubescent. The color of the leaves is medium green.

Branching: Plants of watermelon line SP-4 are heavily branched (also referred to as "lacy vined"), having significantly more branches than the variety referred to as Sangria™. The lacy vine characteristic enables the pollenizer to produce more accessible male flowers, thereby enhancing exposure of the flowers to bees.

Fruit: The fruit rind of plants of watermelon line SP-4 is very brittle and is easily broken. The brittle fruit rind splits easily, due to maturation or by breaking or splitting of the fruit during harvest of the seedless triploid watermelon. Splitting of fruit signals the plant that it hasn't completed its reproductive process inducing the plant to continue flowering for a longer period of time. Brittleness is conferred by a gene e (explosive rind, thin, and tender rind, bursting when cut (Rhodes & Dane, 1999, *Gene List for Watermelon*, Cucurbit Genetics Cooperative Report 22:71-77). The thickness of the rind is approximately 5 mm at the blossom end and approximately 7 mm at the sides of the fruit.

The size of mature fruits of plants of watermelon line SP-4 is approximately 18 cm long and 16 cm wide (diameter at midsection). Small fruit size, as well its brittleness was selected to decrease the load on the plant, thereby extending the duration of plant growth and flower production. Another advantage of the small fruit size is that it enables the harvester to easily distinguish the seedless fruit from seeded fruit, is often difficult with most currently used pollenizers, which are selected based on their overall similarity to the seedless triploid plants. Fruits of watermelon line SP-4 are slightly grooved, their color is mottled/netted. The primary color of the fruit is light green (Charleston Grey), the secondary color medium green (Sugar Baby).

The flesh of the fruits of watermelon line SP-4 is soft, with fine-little fiber. Its color is white. In one embodiment, the percentage of soluble solids of juice taken from the center of the fruit is approximately 7% (compared to approximately 12% for variety Mickylee). The fruits of watermelon line SP-4 have typically no hollow heart, no placental separation and no transverse crack.

Flowering: The plants of watermelon line SP-4 also flower approximately 7 to 10 days earlier than most diploid pollenizer plants currently used for the production of seedless watermelon, and continue flowering during fruit harvest time of the seedless watermelon, 2 to 3 weeks longer than most standard diploid pollenizer plants. Thus, the pollenizer plant of the invention has a flowering duration that is approximately 3 to 5 weeks longer than most pollenizers currently used. Staminate and perfect flowers have a width of approximately 2 cm (across the flower). The color of the flowers is yellow.

Seeds: Seeds of watermelon line SP-4 are approximately 6 mm long, approximately 4 mm wide and approximately 2 mm thick. Their color is dark brown mottled. 1,000 seeds of watermelon line SP-4 weigh approximately 17 grams. There are approximately 660 seeds per fruit.

Other Traits: Watermelon line SP-4 can be used either as donor of the set of traits disclosed above, or as the recurrent parent to develop additional pollenizer lines. These traits are for example disease resistance (e.g. Gummy Stem Blight, Powdery Mildew, and Bacterial Fruit Blotch), insect resistance (e.g. cucumber beetle, aphids, white flies and mites), salt tolerance, cold tolerance and/or herbicide resistance added. These traits can be added to existing lines by using either conventional backcrossing method, pedigree breeding method or genetic transformation. The methods of conventional watermelon breeding are taught in several reference books, e.g. Maynard, D. N. (editor), 2001, WATERMELONS Characteristics, Production and Marketing, ASHS Press; Mohr, H. C., Watermelon Breeding, in Mark J. Bassett (editor), 1986, Breeding Vegetable Crops, AVI Publishing Company, Inc. General methods of genetic transformation can be learned from publish references, e.g. Glich et al., (Eds), 1993, Methods in Plant Molecular Biology & Biotechnology, CRC Press.

Method of Seedless Watermelon Production: Commercial seedless watermelon growers in NAFTA often use elongated diploid varieties with an Allsweet stripe pattern: light green skin with wide green stripes, as the pollenizer. The variety referred to as Sangria™ is one of the most preferred Allsweet type pollenizer and is available as a commercial product from Syngenta Seeds, Inc., Boise Id. Typically, the pollenizer is inter-planted with the triploid watermelon either between rows or within row. The current methods of planting diploid pollenizers often include planting the diploid plants at a distance from adjacent triploid such that they have the same field area available per plant as the field area that is available to the triploid watermelon plants. For example, currently watermelon growers may inter-plant the diploids within a row, whereby the space between all adjacent plants within the row are approximately equidistant.

Alternatively, diploid pollenizer plants are planted in separate rows between rows of triploid watermelon plants. All rows of diploid and triploid plants in such a field are planted approximately equidistant from each other. In other words, under current methods for producing seedless watermelon, the width of all diploid and triploid rows is often the same.

The method of the present invention includes planting plants of watermelon line SP-4 in rows that are narrower than the triploid rows, thereby saving field area for production of triploid seedless watermelon.

EXAMPLE 1

Triploid watermelon plants are planted in parallel rows 7 feet apart and 3 feet apart within each row. However, plants of watermelon line SP-4 are planted in a narrow row 3.5' wide (½ the width of the triploid rows) between every second and third triploid row. For example, rows A and B are two consecutive rows of triploids, each 7-foot wide. Row C is a diploid row that is 3.5 feet wide. Row D and E are the following two 7 foot wide rows of triploids, followed by the 3.5-foot wide row F of diploid plants. This pattern is repeated across the width of the field. Because the diploid row is narrower according to the method of the invention, the distance between rows B and D is 10.5 feet instead of a traditional distance of 14 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

EXAMPLE 2

Triploid watermelon plants are again planted in parallel rows 7 feet apart and 3 feet apart within each row. As in Example 1, plants of watermelon line SP-4 are planted in a narrow row 3.5' wide, but are planted between every third and fourth triploid row. For example, rows A, B, and C, are three consecutive rows of triploids, each row being 7' wide. The following row D is a diploid row that is 3.5 feet wide. Row E, F, and G are the following three rows of triploids, all 7 feet wide, followed by a 3.5 foot wide row of plants of watermelon line SP-4. This pattern is repeated across the width of the field. Because the diploid row is narrower according to the method of the invention, the distance between rows B and D is again 10.5 feet instead of a traditional distance of 14 feet. Using this ratio of 1 pollenizer row for every 3 triploid rows (1:3), 25% of the field would normally be used for the pollenizer plants. Reducing the width of the pollenizer row according to the method of the invention by one-half, the gain of space for planting additional triploid plants would be 25%/2 or approximately 12%.

EXAMPLE 3

Triploid watermelons are planted in parallel rows 8 feet apart and 3 feet apart within each row. Plants of watermelon line SP-4 are planted in a narrow row 4.0 feet wide (½ the width of the triploid rows) between every second and third triploid row. For example, rows A and B are two consecutive rows of triploids, each 8 foot wide. Row C is a diploid row that is 4.0 feet wide. Row D and E are the following two 8 foot wide rows of triploids, followed by the 4.0 foot wide row F of diploid plants. This pattern is repeated across the width of the field. Because the diploid row is narrower according to the method of the invention, the distance between rows B and D is 12.0 feet instead of a traditional distance of 16 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

EXAMPLE 4

Referring to the above three examples, when triploids are planted in rows 8 feet apart, and the ratio of diploid to triploid is 1:3, it is now clear that the reduction of the pollenizer row width by one-half will gain space for planting additional 12%.

EXAMPLE 5

It is also within the scope of the invention to reduce the pollenizer row width to approximately ⅓ that of the triploid row width. Thus, according to the present invention, at any row width, when the ratio of diploid rows to triploid rows is:
  (a.) 1:2, the savings of field area for additional triploid plants is (33%×⅔) or 22%.
  (b) 1:3, the savings of field area for additional triploid plants is (25%×⅔) or 16.5%.
  (c) 1:4, the savings of field area for additional triploid plants is (20%×⅔) or 13.2%.

It is also within the scope of the invention to reduce the pollenizer row width to approximately ⅔ that of the triploid row width.

EXAMPLE 6

It is also within the scope of the present invention to inter-plant the diploid plants within the rows of triploid plants. According to the invention, the triploid plants are first planted by machine or by hand in regularly spaced rows. The triploid plants within each row are planted, for example, 3 feet apart.

After the triploid plants are in the field as described, the diploid pollenizer watermelon plants of the invention are inter-planted, by hand, within each row approximately midway between the triploid plants. Thus, in this example, the diploid plants are planted approximately 1.5 feet from the flanking triploid plants within the row. Due to the characteristics of watermelon line SP-4, the diploid plants can be inter-planted within each row after every 2, 3, 4, 5, 6, 7, 8, 9, or 10 consecutive triploid plants. It is currently preferred in the industry to plant the diploid plants after every 2 (1:2) or 3 (1:3) triploid plants within the row. An 1:4 ratio has been reported, but is not normally used in commercial fields due to inadequate pollenization of the triploid plants. The field area saved under this example, when compared with both the current methods of planting diploids in separate rows or within a row at the ratios (diploid:triploid) of:
  (a) 1:2, is 33.3%,
  (b) 1:3, is 25%,
  (c) 1:4, is 20%.

Methods of the present invention comprises planting plants of watermelon line SP-4 in rows that are narrower than the rows containing the triploid plants. Although the narrower row will encourage growth of plants of watermelon line SP-4 into the triploid plant row, the characteristics of watermelon line SP-4 allow it maintain its ability to sufficiently pollinate the triploid plants in the field. Thus, watermelon line SP-4 and method of the present invention increase the yield of seedless watermelon in a field.

In one aspect, a method of the present invention includes planting a plant of watermelon line SP-4 within a row of triploid watermelon plants. In one embodiment, a method of the present invention includes planting a plant of watermelon line SP-4 and a triploid watermelon plant in the same hole. In one embodiment, plants of watermelon line SP-4 and triploid watermelon plants are planted in a ratio of 3-4:1, i.e. in every $3^{rd}$ or $4^{th}$ hole both a plant of watermelon line SP-4 and a triploid watermelon plant are planted in the same hole. In one embodiment, a plant of watermelon line SP-4 is planted within pollinating distance of a triploid watermelon plant.

EXAMPLE 7

Production of Dihaploid Watermelon Plants

Anthers of watermelon plants are gamma-ray irradiated with cobalt 60 for a dose of 0.4 KGy. Irradiated pollen is gently transferred from the anthers to the receptive stigma on or before anthesis. Each ovary of the pollinated female receives an application of 50 ppm CPPU (a plant cytokinin hormone) to stimulate fruit development. Plants are monitored for pollination take and fruit development. Fruit is harvested 14 days or 21 days post-pollination.

Harvested immature fruit are carefully cut open under sterile conditions and the seeds are meticulously removed from the flesh. The distal portion of each seed is cut off before plating about 40 seeds to each plate of culture medium. Sealed plates with seeds are cultured at 25° C. with a 16-hour photoperiod in a culture room on a Murashige and Skoog Basal Medium, 30 g/L sucrose, 10 g/L agar supplemented either with 10 μM BA (2.25 mg/L) or 22.2 μM BA (5 mg/L) and 2.85 μM IAA (0.5 mg/L), pH 5.8 and dispensed into 100×15 petri dishes after autoclaving.

After 30 days, seeds are screened for greenish immature embryos for embryo rescue. Those with embryos are moved to fresh medium. As the embryos germinated and elongated, they are transferred to small culture jars with the same medium. When sufficient leaf tissue is present on the plantlet, a leaf is sampled and ploidy analysis is carried out by flow cytometry.

Once the plantlets have been confirmed haploid, cuttings/clones are made and rooted in vitro. The medium consists of half strength MS basal salts, 20 g/L sucrose, 1.0 µM IBA (0.2 mg/L), 4 g/L agar and 1 g/L Phytagel, pH 5.8. Once a good root system has developed, plantlets are moved into the greenhouse and planted in trays. The chromosome doubling occurs in the greenhouse by applying 58 µM Surflan (oryzalin) to all apical and axillary nodes. Once plants are established and new flowers exhibit the presence of pollen confirming restored fertility, they are self-pollinated and seed is harvested. Further increase can be done in a field isolated from any other watermelon plant, or physically isolated in a net cage.

DEPOSIT

Applicants have made a deposit of at least 2500 seeds of watermelon line SP-4 with the American Type Culture Collection (ATCC), Manassas, Va., 20110-2209 U.S.A., ATCC Deposit No: PTA-8223. This deposit of watermelon line SP-4 will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC 2321 et seq.).

The foregoing invention has been described in detail by way of illustration and example for purposes of clarity and understanding. However, it will be obvious that certain changes and modifications such as single gene modifications and mutations, somaclonal variants, variant individuals selected from large populations of the plants of the instant watermelon line and the like may be practiced within the scope of the invention, as limited only by the scope of the appended claims. Thus, although the foregoing invention has been described in some detail in this document, it will be obvious that changes and modification may be practiced within the scope of the invention, as limited only by the scope of the appended claims.

All references are incorporated herein in their entities.

What is claimed is:

1. Seed of diploid watermelon line SP-4, wherein representative seed of said line is having been deposited under ATCC Accession No: PTA-8223.

2. A diploid plant of watermelon line SP-4, wherein representative seed of said line is having been deposited under ATCC Accession No: PTA-8223.

3. Pollen of the plant of claim 2.

4. An ovule of the plant of claim 2.

5. Fruit of the plant of claim 2, wherein the fruit is produced by self-pollination of the plant.

6. A method for producing triploid, seedless watermelon fruit, wherein the method comprises the steps of:

a) planting a field with rows of triploid watermelon plants;
b) inter-planting the diploid watermelon plant according to claim 2 within said rows of triploid watermelon plants after every 2nd, 3rd, 4th, 5th, 6th, 7th, 8th, 9th, or 10th triploid plants;
c) allowing pollination of said triploid watermelon plants by pollen of said diploid watermelon plant to obtain triploid, seedless watermelon fruit; and
d) harvesting said triploid, seedless watermelon fruit.

7. A method for producing triploid, seedless watermelon fruit, wherein the method comprises the steps of:

a) planting a field with rows of triploid watermelon plants;
b) planting said field with rows of the diploid watermelon plants according to claim 2, wherein the rows of diploid watermelon plants are approximately one-third to two-thirds the width of the rows of triploid watermelon plants; and
c) allowing pollination of said triploid watermelon plants by pollen of said diploid watermelon plants to obtain triploid, seedless watermelon fruit.

8. The method for producing triploid, seedless watermelon fruit according to claim 7, wherein the rows of diploid watermelon plants are approximately one-half to two-thirds the width of the rows of triploid watermelon plants.

9. The method for producing triploid, seedless watermelon fruit according to claim 7, wherein said rows of diploid watermelon plants are planted after every two rows of triploid watermelon plants.

10. The method for producing triploid, seedless watermelon fruit according to claim 7, wherein said rows of diploid watermelon plants are planted after every three rows of triploid watermelon plants.

11. The method for producing triploid, seedless watermelon fruit according to claim 7, wherein said rows of diploid watermelon plants are planted every four rows of triploid watermelon plants.

12. The method for producing triploid, seedless watermelon fruit according to claim 7, further comprising harvesting said triploid, seedless watermelon fruit.

13. The method for producing triploid, seedless watermelon fruit according to claim 7, wherein the rows of diploid watermelon plants are approximately one-third to one-half the width of the rows of triploid watermelon plants.

14. A method of increasing the yield of triploid, seedless watermelon plants, wherein the method comprises the steps of:

a) obtaining the diploid watermelon plants according to claim 2 for pollenizing said triploid, seedless watermelon plants;
b) planting said diploid watermelon plants in a field of triploid watermelon plants;
c) allowing pollination of said triploid watermelon plants by pollen of said diploid watermelon plants to obtain triploid, seedless watermelon fruit; and
d) harvesting said triploid, seedless watermelon fruit.

15. The method of increasing the yield of triploid, seedless watermelon plants according to claim 14, wherein planting of said diploid watermelon plants is at a ratio of approximately equal to or less than 1 diploid watermelon plant to 2 triploid, seedless watermelon plants.

16. The method of increasing the yield of triploid, seedless watermelon plants according to claim 14, wherein planting of said diploid watermelon plants is at a ratio of approximately equal to or less than 1 diploid watermelon plant to 4 triploid, seedless watermelon plants.

17. A method for producing seeds of a watermelon plant, wherein the method comprises the steps of:

a) growing in a field the watermelon plant according to claim 2;
b) conducting pollination of said plant; and
c) harvesting seed of said plant.

18. The method according to claim 17, further comprising drying said seed.

19. A method for producing a hybrid watermelon variety, wherein the method comprises the steps of:
a) planting in a field a first and a second watermelon plant, wherein said first watermelon plant is the male parent, wherein said second watermelon plant is the female parent, and wherein said first or said second watermelon plant is the watermelon plant according to claim 2;
b) conducting pollination between said first and second watermelon plants; and
c) harvesting seed from said female parent, wherein said seed is seed of a hybrid watermelon variety.

20. A method for producing triploid, seedless watermelon fruit, wherein the method comprises the steps of:
a) interplanting the diploid watermelon plant according to claim 2 and triploid watermelon plants in a field; and
b) allowing pollination of said triploid watermelon plants by pollen of said diploid watermelon plant to obtain triploid, seedless watermelon fruit.

21. The method for producing triploid, seedless watermelon fruit according to claim 20, further comprising harvesting said triploid, seedless watermelon fruit.

22. A method for producing triploid, seedless watermelon fruit, wherein the method comprises the steps of:
a) interplanting seed of the diploid watermelon line according to claim 1 and triploid watermelon plants in a field;
b) allowing said seed to grow into diploid watermelon plants; and
c) allowing pollination of said triploid watermelon plants by pollen of said diploid watermelon plants to obtain triploid, seedless watermelon fruit.

23. A method for producing triploid, seedless watermelon fruit, wherein the method comprises the steps of:
a) interplanting the diploid watermelon plants according to claim 2 and seed of triploid watermelon plants in said field,
b) allowing said seed to grow into triploid watermelon plants; and
c) allowing pollination of said triploid watermelon plants by pollen of said diploid watermelon plants to obtain triploid, seedless watermelon fruit.

24. A method for producing triploid, seedless watermelon fruit, wherein the method comprises the steps of:
a) interplanting seed of the diploid watermelon line according to claim 1 and seed of triploid watermelon plants in a field;
b) allowing said seed to grow into diploid watermelon plants and triploid watermelon plants, reaspectively; and
c) allowing pollination of said triploid watermelon plants by pollen of said diploid watermelon plants to obtain triploid, seedless watermelon fruit.

\* \* \* \* \*